US00PP34024P3

(12) United States Plant Patent
Schoone

(10) Patent No.: US PP34,024 P3
(45) Date of Patent: Mar. 15, 2022

(54) ***PHALAENOPSIS* PLANT NAMED 'GRAND DESSERT'**

(50) Latin Name: *Phalaenopsis hybrida*
Varietal Denomination: Grand Dessert

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,965

(22) Filed: Jun. 5, 2021

(65) Prior Publication Data

US 2021/0385991 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on phalaenopsis plant named, 'Grand Dessert', QZ PBR 2019/0713, filed Mar. 15, 2019.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'Grand Dessert', characterized by its relatively compact and upright plant habit; moderately vigorous to vigorous growth habit; strong flowering stems; strong leaves; freely flowering habit with typically two inflorescences per plant, each inflorescence with numerous flowers; large white-colored flowers; and good postproduction longevity.

2 Drawing Sheets

Figure 1:
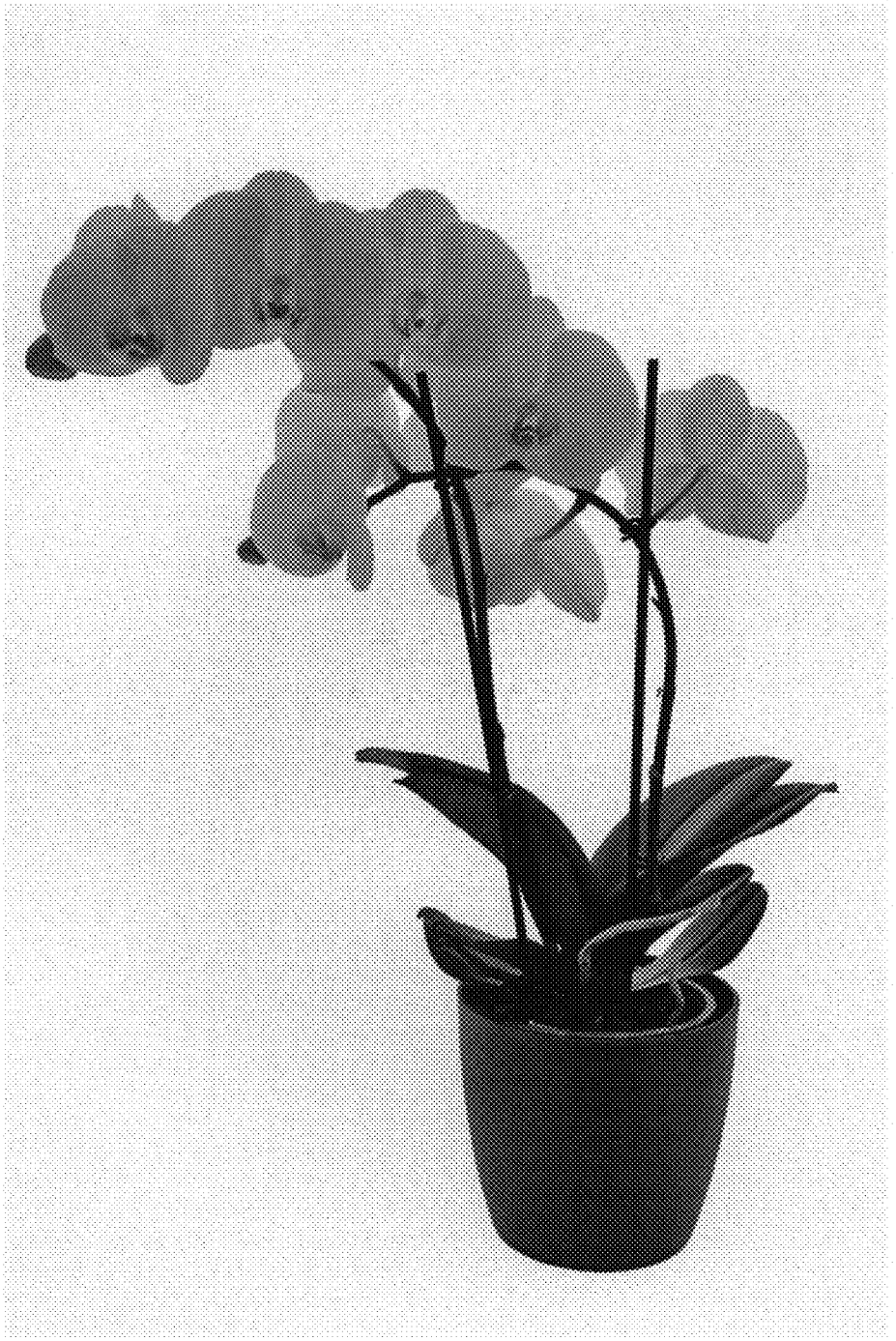

Botanical designation: *Phalaenopsis hybrida.*
Cultivar denomination: 'GRAND DESSERT'.

CROSS-REFERENCED TO CLOSELY-RELATED APPLICATIONS

Title: Varieties of *Phalaenopsis* Plants
Inventor: René Schoone
Filed: Jun. 6, 2020
Ser. No. 62/705,003
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Mar. 15, 2019, application number 2019/0713. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Grand Dessert'.

The new *Phalaenopsis* plant is a product of a planned breeding program conducted by the Inventor in Den Hoorn and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in January, 2011 in Den Hoorn, The Netherlands of a proprietary selection of *Phalaenopsis hybrida* identified as code number ST 3724, not patented, as the female, or seed, parent with a proprietary selection of *Phalaenopsis hybrida* identified as code number ST 4031, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in March, 2017.

Asexual reproduction of the new *Phalaenopsis* plant by in vitro meristem propagation in a controlled environment in Assendelft, The Netherlands since March, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Grand Dessert'. These characteristics in combination distinguish 'Grand Dessert' as a new and distinct *Phalaenopsis* plant:

1. Relatively compact and upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Large white-colored flowers.
7. Good postproduction longevity.

Plants of the new *Phalaenopsis* can be compared to plants of the female parent selection. Plants of the new *Phalaenopsis* differ primarily from plants of the female parent selection in plant habit as plants of the new *Phalaenopsis* are half as tall as plants of the female parent selection. In addition, peduncles of plants of the new *Phalaenopsis* have more anthocyanin development than peduncles of plants of the female parent selection.

Plants of the new *Phalaenopsis* can be compared to plants of the male parent selection. Plants of the new *Phalaenopsis* differ primarily from plants of the male parent selection in plant habit as plants of the new *Phalaenopsis* are much shorter than plants of the male parent selection. In addition, peduncles of plants of the new *Phalaenopsis* have more anthocyanin development than peduncles of plants of the male parent selection.

Plants of the new *Phalaenopsis* can be compared to plants of *Phalaenopsis hybrida* 'Dolce Gelato', not patented. In side-by-side comparisons, plants of the new *Phalaenopsis* differ primarily from plants of 'Dolce Gelato' in the following characteristics:

1. Plants of the new *Phalaenopsis* are shorter than plants of 'Dolce Gelato'.
2. Plants of the new *Phalaenopsis* have slightly larger flowers than plants of 'Dolce Gelato'.
3. Peduncles of plants of the new *Phalaenopsis* have more anthocyanin development than peduncles of plants of 'Dolce Gelato'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Grand Dessert' grown in a container.

Figure 2:
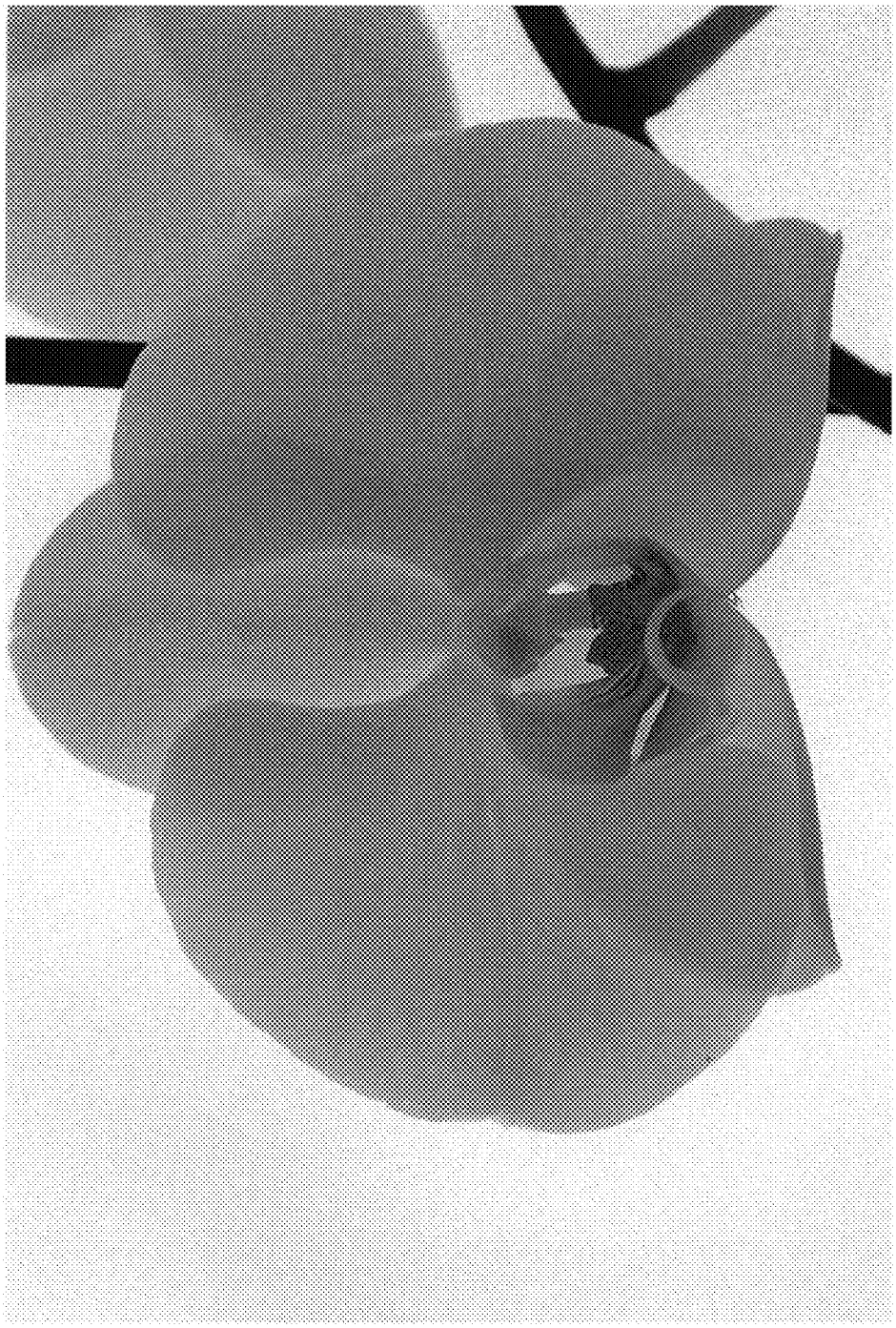

The photograph on the second sheet (FIG. 2) is a close-up view of a typical flower of 'Grand Dessert'.

DETAILED BOTANICAL DESCRIPTION

The aforementioned photographs and following observations and measurements describe plants grown during the early winter in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Grand Dessert'.

Parentage:

*Female parent*.—Proprietary selection of *Phalaenopsis hybrida* identified as code number ST 3724, not patented.

*Male parent*.—Proprietary selection of *Phalaenopsis hybrida* identified as code number ST 4031, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; relatively compact and upright plant habit with typically two inflorescences per plant, each inflorescence with numerous flowers; monopodial; moderately vigorous to vigorous growth habit and moderate growth rate.

*Plant height, substrate level to top of foliar plane*.—About 12.1 cm.

*Plant height, substrate level to top of inflorescences*.—About 36.6 cm.

*Plant diameter or spread*.—About 24 cm.

Leaf description:

*Arrangement and quantity*.—Distichous, simple; sessile; about eight leaves per plant.

*Length*.—About 12.2 cm.

*Width*.—About 6.5 cm.

*Aspect*.—Upright to outwardly arching.

*Shape*.—Broadly elliptic to obovate; moderately carinate.

*Apex*.—Unequal broadly acute to unequal obtuse.

*Base*.—Sheathing. Sheath length: About 1.2 cm. Sheath width: About 1.3 cm. Sheath color: Close to 143B to 143C; towards the distal margin, close to 143A.

*Margin*.—Entire; slightly revolute.

*Texture and luster, upper surface*.—Smooth, glabrous; moderately glossy.

*Texture and luster, lower surface*.—Smooth, glabrous; slightly glossy.

*Venation pattern*.—Camptodromous.

*Color*.—Developing leaves, upper surface: Close to 137A. Developing leaves, lower surface: Close to 146B. Fully expanded leaves, upper surface: Close to 137A to 137B; venation, close to 144A. Fully expanded leaves, lower surface: Close to between 144A and 146B; venation, close to 137B.

Inflorescence description:

*Appearance and flowering habit*.—Showy zygomorphic flowers arranged on axillary branched racemes; typically two inflorescences per plant; each inflorescence with about eight flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 22.6 cm.

*Inflorescence width*.—About 13.7 cm.

*Flower buds*.—Height: About 2.1 cm. Diameter: About 1.6 cm by 2 cm. Shape: Broadly ovate. Color: Close to between 145B and 150B.

*Flower size*.—Large, about 8 cm (vertical) by 9.2 cm (horizontal).

*Flower depth*.—About 3 cm.

*Petals, quantity and arrangement*.—Three, two lateral petals and one center petal transformed into a labellum.

*Lateral petals*.—Length: About 4.5 cm. Width: About 6.3 cm. Shape: Reniform to lunate. Apex: Shallowly retuse. Margin: Entire. Texture and luster, upper and lower surfaces: Smooth, glabrous, velvety; matte. Color: When opening, upper surface: Close to NN155B. When opening, lower surface: Close to 157D; center and towards the margins, close to NN155B. Fully opened, upper and lower surfaces: Close to NN155D; color does not change with subsequent development.

*Labella*.—Appearance: Three-parted with two lateral lobes and a central lobe. Length, lateral lobes: About 2.2 cm. Width, lateral lobes: About 1.5 cm. Length, central lobe: About 3.7 cm. Width, central lobe: About 7 mm to 21 mm. Shape, lateral lobes: Obovate. Shape, central lobe: Deltoid. Apex, lateral lobes: Obtuse. Apex, central lobe: Cleft with two narrow and strongly recurved cirrose tips, about 2 cm in length and about 1.6 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 7 mm in width and about 5 mm in height. Color: When opening, upper surface: Lateral lobes: Close to NN155D; basal margin, close to 12B; towards the base, axillary stripes, close to 182B and 182C. Central lobe: Close to NN155B; broad area and main vein, close to 1A and 1B; towards the margins, close to 174B; at the base (at column connection), close to NN155C with radial stripes, close to 181A to 181B; cirrose tips, close to NN155B and 4D. Callosities: Close to 15A; fine dots, close to 178B. When opening, lower surface: Lateral lobes: Close to NN155D; basal margin, close to 8A; towards the base, close to 156C. Central lobe: Close to 157A; broad area, close to 1A and 1B; towards the margins, close to NN155D and at the edges, close to 174B; at the base (at column connection), close to 156C and 185D; main vein, close to 145B to 145C; cirrose tips, close to NN155B and 4D. Fully opened, upper surface: Lateral lobes: Close to NN155D; basal margin, close to 13B; towards the base, axillary stripes, close to 178B. Central lobe: Close to NN155B; broad area and main vein, close to 7C; towards the margins, close to 173B; at the base (at column connection), close to NN155A with radial stripes, close to 181A to 181B; cirrose tips, close to NN155B and 4D. Callosities: Close to 15A; fine dots, close to 178B. Fully opened, lower surface: Lateral lobes: Close to NN155D; basal margin, close to 12B; towards the base, close to 156C. Central lobe: Close to 157A; broad area, close to 1B; towards the margins, close to NN155D and at the edges, close to 173B; at the base (at column connection), close to 156C and 185D; main vein, close to 145C; cirrose tips, close to NN155B and 4D.

*Sepals*.—Quantity and arrangement: Three, one upper dorsal sepal and two lower lateral sepals. Length, dorsal sepal: About 4.4 cm. Width, dorsal sepal: About 3.9 cm. Length, lateral sepals: About 4.8 cm. Width, lateral sepals: About 3.4 cm. Shape, dorsal sepal: Broadly elliptic to slightly obovate. Shape, lateral sepals: Ovate. Apex, dorsal sepal: Shallowly emarginate. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to NN155C; towards the base, slightly tinged with close to 157D. When opening, lower surface: Close to between 150D and 157A; towards the margins, close to NN155B. Fully opened, upper surface: Close to NN155D. Fully opened, lower surface: Close to NN155D; towards the base, tinged with close to 157D; main vein, distally, slightly tinged with close to 186D. Color, lateral sepals: When opening, upper surface: Close to 157D to lighter than 157D; towards the apex, close to 155C; towards the base, close to 157A. When opening, lower surface:

Close to between 150D and 157A; towards the apex, tinged with close to 182D; towards the base, close to 145C; venation, close to 145B. Fully opened, upper surface: Close to NN155D; towards the base, close to 157D. Fully opened, lower surface: Close to NN155D; towards the base, close to 157D and at the base, close to 157A; main vein, distally, tinged with close to 186D.

*Peduncles*.—Length: About 39.6 cm. Diameter: About 6 mm. Strength: Strong. Aspect: Upright to outwardly arching. Texture and luster: Smooth, glabrous; matte. Color: Close to 146A to 146B, densely covered with fine dots, close to between N186C and 200A.

*Pedicels*.—Length: About 4 cm. Diameter: About 4 mm. Strength: Moderately strong. Aspect: About 80° from peduncle axis. Texture and luster: Smooth, glabrous; matte. Color: Close to 144C; distally, close to 154D and proximally, close to between 146A and 148A.

*Reproductive organs*.—Androecium: Column length: About 8 mm. Column width: About 7 mm. Column color: Close to NN155B. Pollinia quantity: Two. Pollinia diameter (per two pollinia): About 2.25 mm. Pollinia color: Close to 25B. Gynoecium: Stigma length: About 4 mm. Stigma width: About 6 mm. Stigma shape: Reniform. Stigma color: Close to 157B. Ovary length: About 7 mm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Grand Dessert' as illustrated and described.

* * * * *